United States Patent

Carlson

[19]

[11] Patent Number: 5,977,546

[45] Date of Patent: Nov. 2, 1999

[54] SELF NORMALIZING RADIANT ENERGY MONITOR AND APPARATUS FOR GAIN INDEPENDENT MATERIAL QUANTITY MEASUREMENTS

[76] Inventor: Lee Richard Carlson, 2260 Crestline Rd., Pleasanton, Calif. 94566

[21] Appl. No.: 08/855,121

[22] Filed: May 13, 1997

[51] Int. Cl.[6] .................................................. G01N 21/17
[52] U.S. Cl. .................... 250/339.13; 250/343; 250/345; 250/575; 250/373; 356/433; 356/436; 356/437
[58] Field of Search .............................. 250/339.13, 343, 250/345, 575, 373; 356/433, 436, 437

[56] References Cited

U.S. PATENT DOCUMENTS

| | | |
|---|---|---|
| 3,562,522 | 2/1971 | Cederstrand et al. . |
| 3,745,349 | 7/1973 | Liston . |
| 3,807,876 | 4/1974 | Nakahara et al. . |
| 3,811,776 | 5/1974 | Blau . |
| 3,895,233 | 7/1975 | Boll et al. . |
| 4,057,734 | 11/1977 | Barringer . |
| 4,233,513 | 11/1980 | Elder et al. . |
| 4,300,049 | 11/1981 | Sturm . |
| 4,355,234 | 10/1982 | Fertig et al. . |
| 4,500,207 | 2/1985 | Maiden . |
| 4,525,627 | 6/1985 | Krempl et al. ........................... 250/345 |
| 4,598,201 | 7/1986 | Fertig et al. . |
| 4,648,396 | 3/1987 | Raemer . |
| 4,682,031 | 7/1987 | Fabinski et al. . |
| 4,975,582 | 12/1990 | Mount et al. . |
| 5,077,469 | 12/1991 | Fabinski et al. . |
| 5,153,436 | 10/1992 | Apperson et al. . |
| 5,239,492 | 8/1993 | Hartwig et al. . |
| 5,341,214 | 8/1994 | Wong . |
| 5,381,010 | 1/1995 | Gordon . |
| 5,517,314 | 5/1996 | Wallin ..................................... 356/437 |
| 5,679,955 | 10/1997 | Schmidt et al. ........................ 250/343 |

FOREIGN PATENT DOCUMENTS

90177445 U  12/1991  Germany .

OTHER PUBLICATIONS

WO 95 25950 (Andros Inc.) Sep. 25, 1995.

*Primary Examiner*—Constantine Hannaher
*Assistant Examiner*—Andrew Israel
*Attorney, Agent, or Firm*—Frederick K. Lacher; Marcella R. Louke

[57] ABSTRACT

Method and apparatus for measuring the quantity of sample materials which provides stable measurements for extended periods of time. A source beam containing measuring radiation and reference radiation is directed through a sample material. The measuring radiation consists of spectral energy that interacts substantially with the sample material. The reference radiation consists of spectral energy with substantially different interaction properties with the sample material. Radiation is directed along separate analyzing and normalizing information channels wherein the radiation has substantially different sample interaction. Analyzing and normalizing detectors provide responses to radiation in respective analyzing information channel or normalizing information channel. A measuring mode is established by inserting a first filter into the source beam to allow substantially only measuring radiation to propagate to the detectors, creating measuring responses. A normalizing mode is established by inserting a second filter into the source beam to allow substantially only reference radiation to propagate to the detectors, creating normalizing responses. The detector responses are used collectively with appropriate signal processing means to obtain a measurement of sample quantity which is substantially independent from variations in measuring radiation intensity, variations in reference radiation intensity, changes in optical collection efficiencies for both detectors, and changes in gain from the response signals from both detectors.

4 Claims, 3 Drawing Sheets

SELF NORMALIZING RADIANT ENERGY MONITOR AND APPARATUS FOR GAIN INDEPENDENT MATERIAL QUANTITY MEASUREMENTS

BACKGROUND OF THE INVENTION

1. Field of Invention

This invention pertains to the art of methods and apparatuses for measuring the quantity of a sample material utilizing photometric means, and more specifically to methods and apparatuses for obtaining and processing detector responses to both measuring and reference radiation.

2. Description of the Related Art

The measurement of material quantities is important in many industrial, medical, and domestic applications. The use of light interaction with sample materials provides a convenient, low cost, and reliable measuring technology known as photometry. The principles of photometry are well known in the art. The Beer-Lambert law of absorption is given below:

$$\frac{I(\lambda)}{I(\lambda)_o} = e^{-\sigma(\lambda)nl} \qquad (1)$$

where $I(\lambda)_O$ is the radiation intensity at a specified wavelength measured when no absorbing material is present; $I(\lambda)$ is the measured radiation intensity at a specified wavelength after $I(\lambda)_O$ is passed through the sample material, $\sigma(\lambda)$ is the probability of radiation absorption by the sample material at the wavelength $\lambda$; n is the quantity of material to be measured; and l is the distance the radiation travels in the material medium. Under ideal conditions of a collimated monochromatic source with constant radiation intensity and a well defined path length of radiation, the Beer-Lambert law provides a convenient means of measuring the quantity of material in a sample.

The difficulties associated with a practical photometer include establishing a radiation source with a constant radiation flux at a detector at a specified radiation wavelength or band of wavelengths and a stable response from the radiation detector. It is well known to one skilled in the art that physical and chemical changes in the source construction over time cause changes in source radiation intensities. Contamination deposits on the surface of optical components also attenuate radiation intensities, and physical movement of radiation sources and/or optical elements change the radiation flux striking measuring detectors. The measurement process is further biased by signal response produced by radiation detectors sensitivities due to aging or from temperature changes, and variations in signal gain from the signal conditioning electronics are common.

Photometer response measurements can be described in terms of radiation production, non-sample material related radiation loss, sample material related radiation loss, and detector response factors as follows:

$$R^{Op} = I^{Op} * F^{Op} * L^{Op} * D^{Op} * G^{Op} * X(n)^{Op} \qquad (2)$$

where I represents the source radiation intensity at a specified measuring wavelength or band of wavelengths; F is the fraction of radiation directed from the radiation source to the radiation detector; L is the fraction of light directed to the detector not absorbed by contamination materials; D is the sensitivity of the radiation detector to the measuring wavelength (detectivity); G is the detector signal conditioning gain; and X is the fraction of radiation not absorbed by the sample material.

When no sample material quantity is present in the measuring instrument, a standard reference response is produced as follows:

$$R = I_0^{St} * F^{St} * L^{St} * D^{St} * G^{St} * X(n_0)^{St} \qquad (3)$$

An instrument response ratio of material quantity measurements to the standard reference of equation (3) gives a material response function, f(mp), as follows:

$$f(mp) = \frac{I^{Op} * F^{Op} * L^{Op} * D^{Op} * G^{Op} * X(n)^{Op}}{I_0^{St} * F^{St} * L^{St} * D^{St} * G^{St} * X(n_0)^{St}} \qquad (4)$$

Factors which are eliminated by cancellation from equation (4) are said to be "common mode". Elimination or minimization of the measurement parameters present in equation (4) that are not dependent on material sample quantities reduces measurement errors and in turn increases the stability of quantitative photometric instruments. As will be shown in the following discussion of the related art, a variety of photometers have been proposed which manipulate the measurement and reference parameters in attempts to design reliable, stable photometers.

Some common instrumentation parameters which change independently of sample material quantities are source intensity, temperature of measuring volumes, temperature of filter devices, temperature of radiation detectors, and pressures of measuring volumes. Attempts have been made in the art to stabilize instrumentation parameters such as the device disclosed in U.S. Pat. No. 4,233,513 to Elder. However, frequent calibration is necessary to overcome changes in the instrument due to physical and chemical changes. Various calibration methods and techniques have been set forth in the art in attempts to overcome such problems.

In general, calibration procedures require interruptions in material monitoring time. Calibration procedures add significant costs to the product design and the operation of the measuring system. In some applications, interruptions of material monitoring can generate unacceptable risk in critical applications such as gas monitors used during medical surgery. Eliminating periodic calibration, or extending the calibration interval will reduce both the time required for measurements and the operating costs.

Other attempts to improve photometric devices have been made by incorporating compensation techniques to the methods and apparatuses. Compensation techniques add measurement variables to photometers which serve to stabilize or correct for measurement parameters which are not intended to change after instrument calibration. For instance, U.S. Pat. No. 4,355,234 to Fertig et al. and U.S. Pat. No. 4,598,201 to Fertig et al. include dual radiation beam configurations which attempt to eliminate instrument drift by adding a reference path to the photometer. Dual beam photometer designs are effective in removing common mode errors due to sample matrix effects, detector response changes and response signal gain changes. The increased design complexity of dual beam instruments generally add significant cost to a photometer design. Dual beam photometers can also increase measurement error due to relative changes in the two beams which arise due to unequal absorption of measuring radiation, contamination of non-optical elements, and mechanical movement of optical elements.

Pressure variations have been employed to create stable signals as described in U.S. Pat. No. 4,500,207 to Maiden and U.S. Pat. No. 4,975,582 to Mount et al. These techniques rely on the long term stability of pressure regulators or pressure modulators to obtain reliable results. However, mechanical components used to generate pressure variations produce undesirable noise, add significant cost, and fail through long term mechanical wear.

Dual wavelength photometers are yet another alternative means to compensate for measuring parameters that are independent from the measured sample material. When adding additional wavelengths to measuring instruments, additional signal responses are obtained. U.S. Pat. No. 5,341,214 to Wong describes a dual wavelength photometer which utilizes a single detector, single beam, and dual wavelengths to analyze gases. However, requirements that intensity ratios of measuring radiations and reference radiations remain constant is a serious limitation to conventional dual wavelength, single beam, single source configurations. Over extended operating periods, radiation source temperatures will change thereby creating changes in measuring and reference radiation intensity ratios. Frequent calibration is therefore required.

In U.S. Pat. No. 3,745,349 to Liston and U.S. Pat. No. 3,895,233 to Boll et al., measuring instruments are disclosed that utilize two radiation sources in order to provide measuring and reference radiation beams with no moving parts. The presence of radiation beams alternate between measuring radiation and reference radiation, which cause measuring signal responses and reference signal responses to be alternately produced. The two radiation sources establish measuring radiation and reference radiation originating from physically distant sources. Relative movement of the sources change light transmission ratios from the measuring radiation source and reference radiation source to the radiation detector. Detectors, and other elements of information channels, are subject to short-term drifts and instabilities that make them respond differently, at different times and in unpredictable ways. When one or both channels exhibit response changes or response components that have no counterpart in the response of the other channel, there is no common mode cancellation of their extrinsic effects on the measurement. Frequent calibration is therefore needed for reliable measurements.

U.S. Pat. No. 4,648,396 to Raemer and U.S. Pat. No. 5,153,436 to Apperson et al. disclose instrumentation with single beams, dual wavelengths, and two detectors. Source radiation containing measuring radiation and reference radiation is directed simultaneously through a sample measuring volume. The measuring radiation and reference radiation are then substantially separated by optical components and directed respectively to measuring radiation detectors and reference radiation detectors. There are no common mode variables in the Raemer and Apperson designs. Apperson et al describe temperature controlled detectors to enhance stability. Raemer relies on the presence or absence of material sample to circumvent the need for frequent calibration. Not all material quantification applications can conveniently remove the sample material at periodic intervals.

U.S. Pat. No. 4,057,734 to Barringer and U.S. Pat. No. 5,381,010 to Gorden disclose dual wavelength, dual beam, dual detector photometers for detecting gases. The monitoring radiation and measuring radiation do not traverse a common optical path but travel in two separate information channels. Therefore, changes in component positions or physical properties that have no counterpart in the response of the other channel can effect one or both information channels to exhibit response changes.

U.S. Pat. No. 4,300,049 to Sturm discloses single source, single path, dual detector, three wavelength instruments for analyzing paper sheet. Although some common mode parameters may be eliminated, the material response function utilized is dependent on the relative spectral sensitivity of the radiation detectors over extended periods of time. Changes in spectral sensitivity will introduce measurement error. Radiation loss due to contamination deposits on optical surfaces will also introduce measurement error in the Sturm photometer. The construction of the instrument is complex, requiring three radiation sources to achieve measuring stability.

The present invention contemplates new and improved methods and apparatuses for obtaining stable and reliable material sample measurements which are simple in design, effective in use, and overcome the foregoing difficulties and others while providing better and more advantageous results.

SUMMARY OF THE INVENTION

In accordance with the present invention, new and improved methods and apparatuses for obtaining reliable and stable quantitative measurements of a sample material are provided.

According to one aspect of the present invention, an apparatus for quantifying a sample gas homogeneously distributed within a sampling zone is provided. The apparatus comprises a radiation source for emitting source radiation including measuring radiation associated with a first wavelength band and reference radiation associated with a second wavelength band; means for directing the source radiation along an initial optical path; a first optical filter being able to substantially transmit reference radiation and substantially block non-reference radiation; a second optical filter being able to substantially transmit measuring radiation and substantially block non-measuring radiation; filtering means for selectively positioning one of the optical filters in the initial optical path of the source radiation whereby filtered radiation selectively continues in the optical path; beam splitting means for splitting the filtered radiation into first and second portions, the first portion being directed along a normalizing optical path and the second portion being directed along an analyzing path, the analyzing path passing at least partially through the sampling zone, the first and second portions having substantially different sample interaction; a normalizing detector positioned in the normalizing optical path for detecting the first potion and creating a normal detector response, $N_R$, when the filtered radiation is the reference radiation and creating a normal detector response, $N_M$, when the filtered radiation is the measuring radiation; an analyzing detector positioned in the analyzing optical path for detecting the second portion and creating an analyzing detector response, $A_R$, when the filtered radiation is the reference radiation and creating an analyzing detector response, $A_M$, when the filtered radiation is the measuring radiation; and, means for processing the normal detector responses and the analyzing detector responses to quantify the sample gas.

According to another aspect of the invention, an apparatus for measuring sample material quantities is provided. The apparatus comprises a radiation source for producing a source radiation containing measuring radiation and reference radiation; a normalizing information channel including a normalizing detector creating outputs responsive to measuring radiation and reference radiation traveling substantially identical optical paths from the radiation source to the normalizing detector; an analyzing information channel including an analyzing detector creating outputs responsive to measuring radiation and reference radiation traveling substantially identical optical paths from the radiation source to the analyzing detector; means for splitting the source radiation into first and second portions and directing the first portions to the normalizing information channel and the second portions to the analyzing information channel, the first and second portions having substantially different sample interaction; means for selectively transmitting substantially only reference radiation from the source to each of the detectors; means for selectively transmitting substantially only measuring radiation from the source to each of the detectors; and, means for processing the outputs from the normalizing and analyzing information channels.

According to yet another aspect of the invention, a method for quantifying a sample gas is provided. The method comprises the steps of providing source means for producing a measuring radiation and a reference radiation; providing means for substantially transmitting only measuring radiation along an optical path; splitting the transmitted measuring radiation into first and second portions; directing the first portion of measuring radiation to a normalizing detector in a normalizing information channel to obtain normalizing detector response, $N_M$; directing the second portion of measuring radiation to an analyzing detector in an analyzing information channel to obtain analyzing detector response, $A_M$; providing means for transmitting substantially only reference radiation along an optical path; splitting the reference radiation into first and second portions; directing the first portion of reference radiation to the normalizing detector in the normalizing information channel to obtain a normalizing detector response, $N_R$, the first portions of measuring and reference radiation having substantially identical first optical paths relative to the sample material; directing the second portion of reference radiation to the analyzing detector in the analyzing information channel to obtain analyzing detector response $A_R$, the second portions of measuring and reference radiation having substantially identical second optical paths relative to the sample material, the first and second optical paths being substantially different; and, processing the detector responses to obtain a sample quantity response, f(mq).

One advantage of the present invention is the provision of a low cost photometric apparatus which achieves substantial long term measuring stability.

Another advantage of the present invention is the novel spectral ratioing technique that minimizes factors which effect material quantity measurements.

Still other benefits and advantages of the invention will become apparent to those skilled in the art to which it pertains upon a reading and understanding of the following detailed specification.

BRIEF DESCRIPTION OF THE DRAWING

The invention may take physical form in certain parts and arrangement of parts, a preferred embodiment of which will be described in detail in this specification and illustrated in the accompanying drawings which form a part hereof and wherein.

DESCRIPTION OF THE PREFERRED EMBODIMENT

Figure 1:
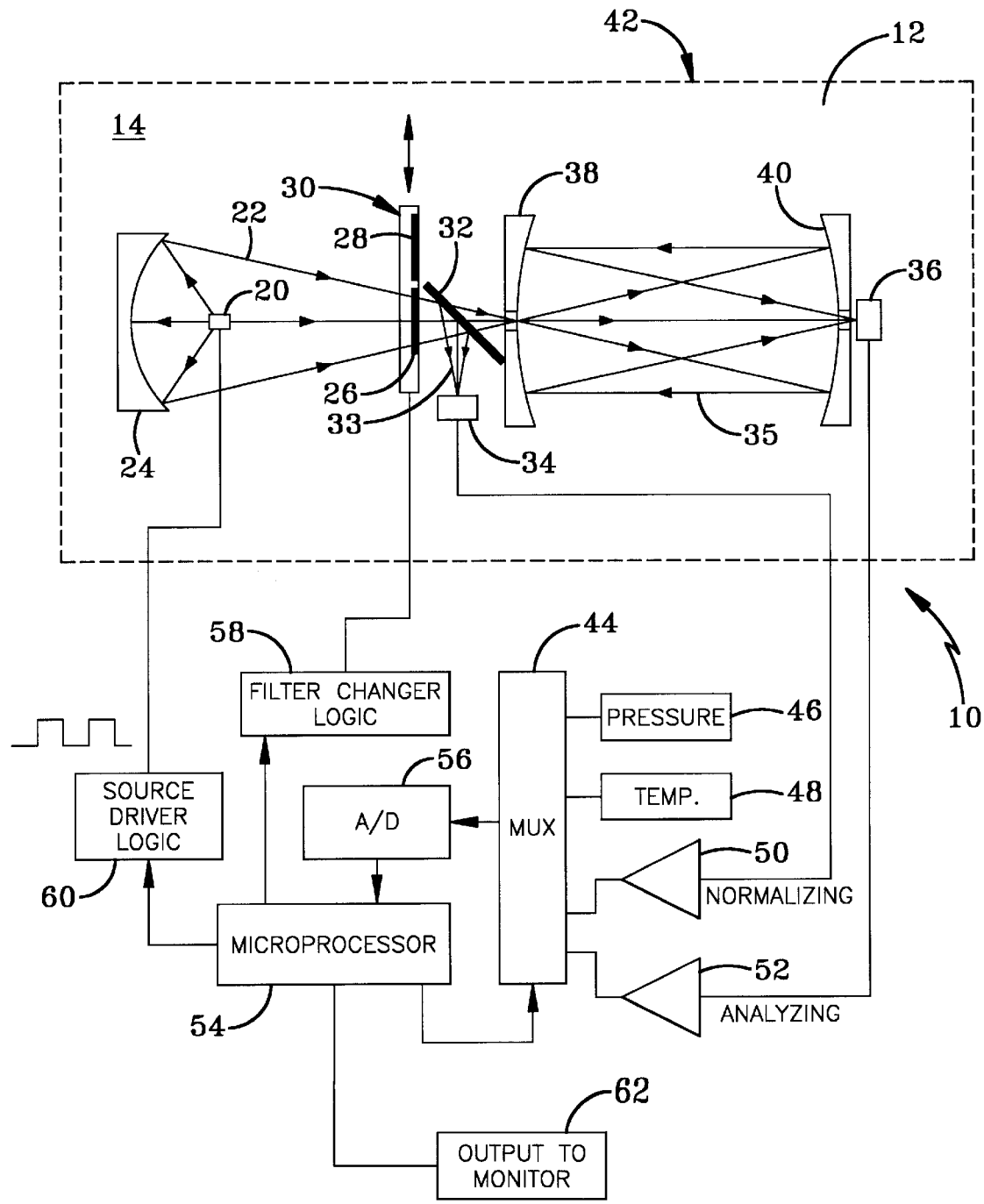
FIG. 1 is a schematic representation of one embodiment of the present invention.
Figure 2:
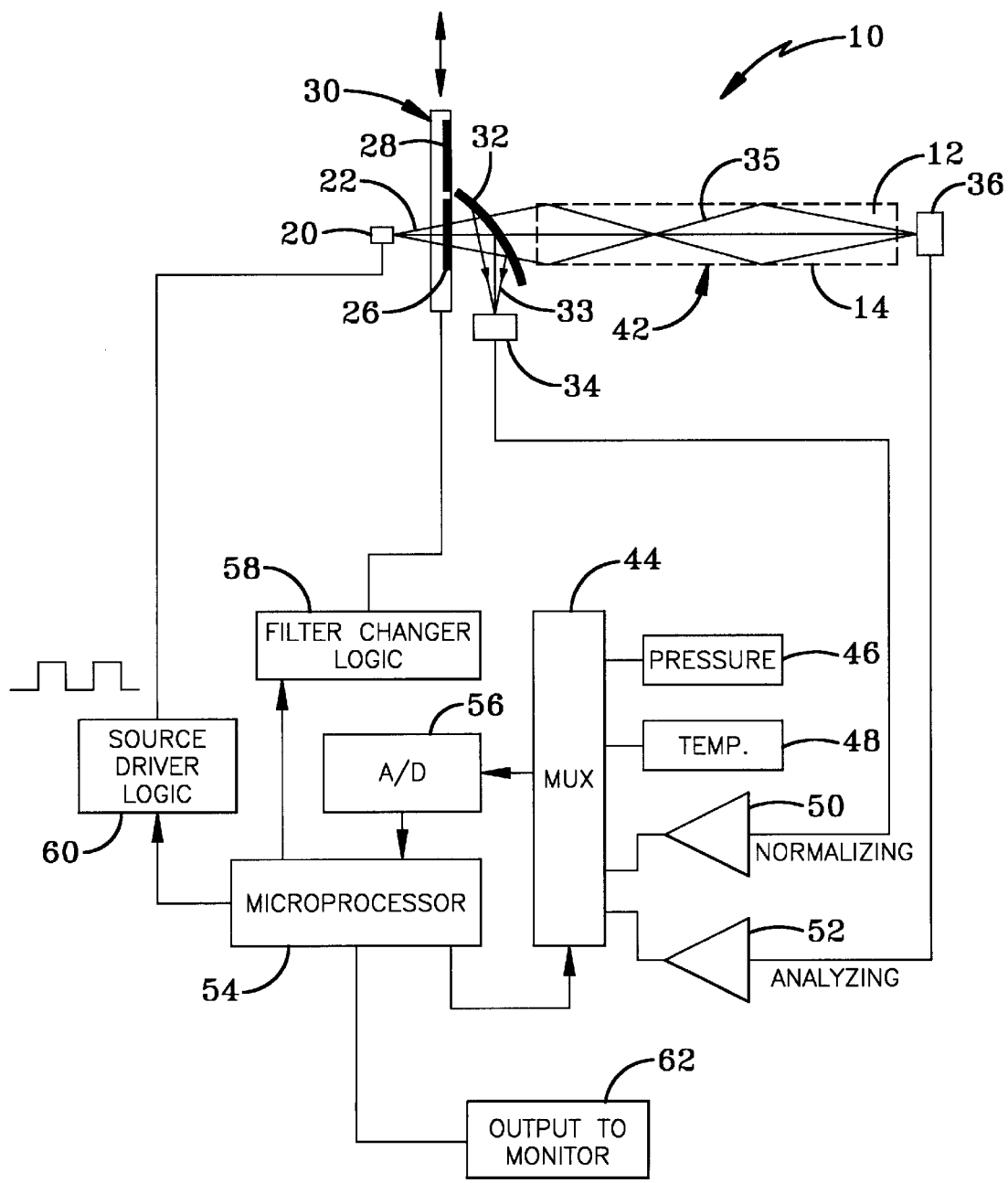
FIG. 2 is a schematic representation of a further embodiment of the present invention.
Figure 3:
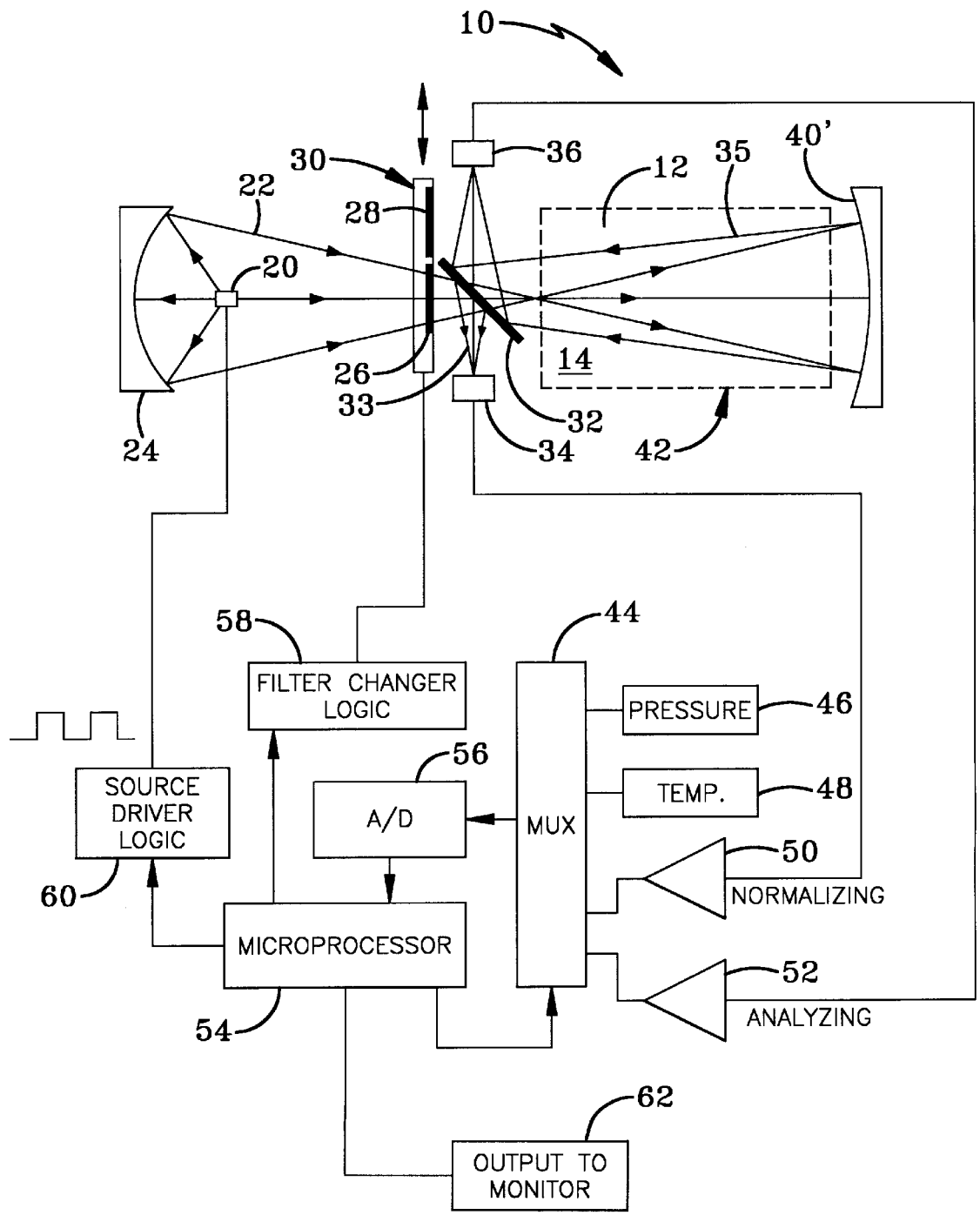
FIG. 3 is a schematic representation of yet another embodiment of the present invention.

Referring now to the drawings wherein the showings are for purposes of illustrating a preferred embodiment of the invention only and not for purposes of limiting the same, FIG. 1 shows a schematic representation of a preferred embodiment of an apparatus 10 for characterizing a sample gas 12. The sample gas 12 is homogeneously distributed within a zone 14 defined by sampling boundary 42. The preferred embodiment of apparatus 10 includes radiation source 20 to produce source radiation 22 indicated by arrows originating from source 20. Radiation source 20 may be located within sampling boundary 42 as shown in FIG. 1. Other embodiments of the invention include radiation source 20 located outside the sampling boundary 42 as shown in FIGS. 2 and 3. Source radiation 22 includes measuring radiation (MR), having an associated measuring radiation waveband length, and reference radiation (RR), having an associated reference radiation waveband length, as will be explained in further detail below. Source radiation 22 is directed toward a filter assembly 30 where it is selectively filtered. With reference to FIG. 1, in a preferred embodiment of the invention, radiation from source 20 is initially directed toward first mirror 24 in order to collect and direct a greater portion of source radiation 22 toward filter assembly 30.

As shown in FIG. 1, filter assembly 30 includes filtering means for selectively filtering source radiation 22. In a preferred embodiment, filter assembly 30 includes first and second optical filters 26, 28 respectively. First filter 26 is substantially transparent to reference radiation (RR) and substantially non-transparent to measuring radiation (MR). In contrast, second filter 28 is substantially non-transparent to reference radiation (RR) and substantially transparent to measuring radiation (MR). Source radiation 22 is alternately transmitted through first and second filters 26 and 28. Either mechanical or electrical means may be employed for effecting a change in the filtering properties of filter assembly 30. In a preferred embodiment, filter changer logic 58 is incorporated into the control system to alternate placement of first and second filters 26, 28 in the optical path of source radiation 22. In the preferred embodiment, first and second filters 26, 28, respectively, are designed to transmit narrow spectral bands of radiation. The choice of filtering properties depends on the application for which the apparatus 10 is intended. For use as an environmental $CO_2$ gas monitoring system, first filter 26 preferably transmits radiation at 3.7 microns and second filter 28 preferably transmits radiation at 4.26 microns. $CO_2$ exhibits a strong absorption feature at 4.26 microns, which is used as the wavelength for measuring radiation. The region of 3.7 microns is transparent to most atmospheric gasses. This wavelength therefore is commonly chosen as a reference band for infrared gas analyzers. The important factor is the ability of filter assembly 30 to alternate between a state of allowing reference radiation (RR) to pass therethrough while blocking measuring radiation (MR) and a state of allowing measuring radiation (MR) to pass therethrough while blocking reference radiation (RR)

For illustrative purposes, a first case as shown in FIG. 1, called "measuring mode" will now be described. The source radiation 22 passes through filter assembly 30. In measuring mode, the filter assembly 30 is arranged, either mechanically or electrically, to employ second filter 28. The source radiation 22 passing through second filter 28 is substantially measuring radiation (MR) at 4.26 microns. The measuring radiation (MR) encounters beam splitter 32. Upon encountering beam splitter 32, a first portion 33 of the measuring radiation (MR) is directed to a normalizing detector 34. A second portion 35 of the measuring radiation (MR) is directed toward an analyzing detector 36. Preferably, first portion 33 and second portion 35 are essentially equal. Silicon is a convenient material to use as beam splitter 32 at the preferred wavelengths.

In a preferred embodiment of the invention, focusing mirror 38 and collimating mirror 40 are positioned to collect and direct a greater fraction of the second portion 35 toward analyzing detector 36. As is apparent from FIG. 1, mirrors 38, 40, respectively, further function to extend the optical path of the measuring radiation (MR) to a distance greater than the physical distance from source 20 to analyzing detector 36. A critical aspect of the invention is the difference in sample interaction between first portion 33 directed toward normalizing detector 34 and second portion 35 directed toward analyzing detector 36. One way to bring about the sample interaction difference is by extending the optical path in either the normalizing or analyzing information channel. In the preferred embodiment, the second portion 35 travels a greater optical distance through the sample gas 12 than first portion 33. Other means of creating a difference in the sample interaction between first portion 33 and second portion 35 are within the scope of the present invention.

In measuring mode, the normalizing detector 34 creates a normalizing detector response for the first portion 33 of measuring radiation, $N_M$. Analyzing detector 36 creates an analyzing detector response for the second portion 35 of measuring radiation, $A_M$.

A second case, called "normalizing mode" will now be described. In normalizing mode, the filter assembly 30 shown in FIG. 1 would be rearranged so that first filter 26 is in the optical path of the source radiation 22 rather than second filter 28. The radiation which passes through first filter 26 is substantially reference radiation (RR) at 3.7 microns. The reference radiation then encounters beam splitter 38. A first portion of reference radiation (RR) follows the same optical path as the first portion 33 of the measuring radiation (MR) described above. The normalizing detector 34 creates a normalizing detector response for the first portion of reference radiation, $N_R$. Likewise, a second portion of reference radiation (RR) follows the same optical path as second portion 35 of the measuring radiation (MR) described above. The analyzing detector 36 creates a analyzing detector response for the second portion of reference radiation, $A_R$.

One important aspect of the present invention is that the normalizing detector 34 creates detector responses for both the measuring radiation (MR) and the reference radiation (RR). Likewise, the analyzing detector 36 creates analyzing detector responses for both the measuring radiation (MR) and the reference radiation (RR).

In the preferred embodiment, source radiation 22 is produced from an incandescent source 20 that utilizes a tungsten filament. Source 20 is operated at approximately 1800° C. producing a broad radiation spectral distribution that is dependent on the blackbody temperature, the emissivity characteristics of the tungsten filament, and the spectral transmission of the glass envelope. Source 20 operates in response to input from source driver logic 60.

In the preferred embodiment, a large fraction of the light from source 20 is collected by first mirror 24. In one embodiment of the invention, first mirror 24 has a 25 mm radius of curvature or 12.5 mm focal length and is positioned 16.5 mm from source 20. As shown in FIG. 1, normalizing detector 34 is positioned at a focal point of the first portion 33 of the source radiation 22 which is directed from beam splitter 32.

In the preferred embodiment, mirrors 38, 40, respectively, are essentially identical, each having a radius of curvature of 80 mm (40 mm focal length) and a 4.5 mm diameter hole positioned on the optical axis. The hole in focusing mirror 38 is positioned at the focal point of the second portion 35 of source radiation 22 which continues through to beam splitter 32. The second portion 35 expands from the focus at focusing mirror 38 to illuminate the entire surface of collimating mirror 40. In the preferred embodiment, mirror 40 is placed 67.6 mm from radiation source 20. Mirror 40 collimates the radiation and directs it back to focusing mirror 38, which directs the radiation through the hole in mirror 40 and focuses it at the analyzing detector 36. Mirrors 38, 40, respectively, are metal coated. The preferred metal is gold at the preferred radiation wavelengths.

Another important aspect of the present invention is the use of measuring radiation (MR) and reference radiation (RR) which are spectrally close together. The normalizing and analyzing detectors 34, 36 respectively, are broad band detectors. It is generally well known in the art that broad band detectors have substantially no detectivity discrimination between spectrally adjacent wavelength bands.

The detector responses, $A_M$, $A_R$, $N_M$, and $N_R$, are electronically processed utilizing signal multiplexer 44, normalizing signal conditioning electronics 50, analyzing signal conditioning electronics 52, digital microprocessor 54, and analog to digital converter 56 to provide output to monitor 62. Sampling conditions read by pressure transducer 46 and temperature transducer 48 are also sent to multiplexer 44.

Using the apparatuses and methods of the present invention, the information provided by $A_M$, $A_R$, $N_M$, and $N_R$ may be processed to produce a normalized material quantity measurement that is substantially independent of gain changes occurring in either the normalizing detector 34, the analyzing detector 36, or both. The normalized material quantity measurement is also substantially independent of intensity and spectral variations in source 20.

The variables $A_M$, $A_R$, $N_M$, and $N_R$ can be expressed as:

$$A_M = I_M * F_A * L_{AM} * D_{AM} * G_A * X_{AM} \tag{5}$$

$$A_R = I_R * F_A * L_{AR} * D_{AR} * G_A * X_{AR} \tag{6}$$

$$N_M = I_M * F_N * L_{NM} * D_{NM} * G_N * X_{NM} \tag{7}$$

$$N_R = I_M * F_N * L_{NR} * D_{NR} * G_N * X_{NR} \tag{8}$$

where:

TABLE 1

| Variable | Variable Representation |
|---|---|
| IM | Intensity of source radiation in the measuring wavelength band |
| $I_R$ | Intensity of source radiation in the reference wavelength band |
| $F_A$ | Fraction of source radiation transmitted and collected at analyzing detector |
| $F_N$ | Fraction of source radiation transmitted and collected at normalizing detector |
| $L_{AM}$ | Fractional loss of measuring radiation due to contamination at analyzing detector |
| $L_{AR}$ | Fractional loss of reference radiation due to contamination at analyzing detector |
| $L_{NM}$ | Fractional loss of measuring radiation due to contamination at normalizing detector |
| $L_{NR}$ | Fractional loss of reference radiation due to contamination at normalizing detector |
| $D_{AM}$ | Detectivity of analyzing detector with measuring radiation |
| $D_{AR}$ | Detectivity of analyzing detector with reference radiation |
| $D_{NM}$ | Detectivity of normalizing detector with measuring radiation |
| $D_{NR}$ | Detectivity of normalizing detector with reference radiation |
| $G_A$ | Analyzing detector gain |
| $G_N$ | Normalizing detector gain |

TABLE 1-continued

| Variable | Variable Representation |
|---|---|
| $X_{AM}$ | Fractional loss of measuring radiation due to material quantity at analyzing detector |
| $X_{AR}$ | Fractional loss of reference radiation due to material quantity at analyzing detector |
| $X_{NM}$ | Fractional loss of measuring radiation due to material quantity at normalizing detector |
| $X_{NR}$ | Fractional loss of reference radiation due to material quantity at normalizing detector |

Sample material quantities may be found by the following relationship:

$$f(mq) = \left\{ \frac{A_M}{A_R} * \frac{N_R}{N_M} \right\} \qquad (9)$$

where f(mq) is a function of the amount of sampling material present. Utilizing the equations (5)–(8) in equation (9) yields the following expression:

$$f(mq) = \left( \frac{I_M * F_A * L_{AM} * D_{AM} * G_A * X_{AM}}{I_R * F_A * L_{AR} * D_{AR} * G_A * X_{AR}} \right) \qquad (10)$$

$$\left( \frac{I_R * F_N * L_{NR} * D_{NR} * G_N * X_{NR}}{I_M * F_N * L_{NM} * D_{NM} * G_N * X_{NR}} \right)$$

Cancellation of common mode variables and rearrangement of terms yields:

$$f(mq) = \left( \frac{D_{AM} * D_{NR}}{D_{AR} * D_{NM}} \right) * \left( \frac{L_{AM} * L_{NR}}{L_{AR} * L_{NM}} \right) * \left( \frac{X_{AM} * X_{NR}}{X_{AR} * X_{NM}} \right) \qquad (11)$$

As is readily apparent, the apparatus of the present invention is substantially independent from variations in $I_M$, $I_R$, $F_A$, $F_N$, $G_A$, and $G_N$.

The first term in Equation (11) relates to the detectivity factors of detectors 34, 36 at the measuring and reference radiations. However, because the chosen wavelengths are spectrally adjacent, $D_{AM}$ and $D_{AR}$ are substantially equal. Likewise $D_{NM}$ and $D_{NR}$ are substantially equal. Therefore, the first term is essentially equal to 1. The present invention requires that the material property interaction of the radiation which is directed to the normalizing detector is the same for both measuring and reference radiation and the material property interaction of the radiation which is directed to the analyzing detector is the same for both measuring and reference radiation. However, the optical path, and hence the material interaction, for the radiation directed to the analyzing detector is substantially different than the material interaction for the radiation directed to the normalizing detector.

Equation (11) therefore reduces to:

$$f(mq) = \left( \frac{L_{AM} * L_{NR}}{L_{AR} * L_{NM}} \right) \left( \frac{X_{AM} * X_{NR}}{X_{AR} * X_{NM}} \right) \qquad (12)$$

The first term in Equation (12) relates to contamination deposits on optical surfaces. The extent to which contamination affects a sample material measurement is dependent on the material properties of contaminants, the quantity of contaminant residue deposited on optical elements, and the number of optical surfaces in the optical path between the source 20 and the detectors 34, 36. Again, because the measuring and reference radiations are spectrally close together, differences in contamination effects between the radiations can be substantially reduced. In addition, minimizing the number of optical surfaces in accordance with the present invention, allows contamination effects to be substantially eliminated. When $L_{AM}$ is substantially equal to $L_{AR}$, and $L_{NM}$ is substantially equal to $L_{NR}$, Equation (12) is effectively reduced to:

$$f(mq) = \left( \frac{X_{AM} * X_{NR}}{X_{AR} * X_{NM}} \right) \qquad (13)$$

The material quantity function is characterized with calibration standards to create a calibration curve. Approximating functions such as polynomials, rational polynomials, or other convenient functions or interpolating algorithms enable comparisons of the calibration curve to measurements of unknown sample quantities.

With reference to FIG. 2, another embodiment of the present invention is shown having the same reference numerals for similar components. Source 20 emits source radiation 22 comprising both reference and measuring radiation at their respective wavelengths. Source radiation 22 is transmitted to filter assembly 30 and passes through either first filter 26 (normalizing mode) or second filter 28 (measuring mode) according to the action of filter changer logic 58. As shown in FIG. 2, the radiation, reference radiation if filter 26 is used or measuring radiation if filter 28 is used, encounters beam splitter 32. First portions 33 are directed to normalizing detector 34 without encountering the sample gas 12. Second portions 35 are directed along a longer optical path within sampling boundary 42 containing sample gas 12 before being focused on analyzing detector 36. Again, detector responses $N_R$, $A_R$, $N_M$, and $A_M$ are processed as in the embodiment shown in FIG. 1 and the sample material is quantified and sent as output to monitor 62.

In the embodiment shown in FIG. 3, first mirror 24 is again positioned to collect and reflect a higher fraction of source radiation 22 toward filter assembly 30. After passing through either first or second filter 26, 28, the radiation encounters beam splitter 32. As in the embodiment shown in FIG. 2, the first portions 33 of the split radiations are directed to normalizing detector 34 outside of the sampling boundary 42. Second portions 35 are directed through sample gas 12 along a longer optical path by reflection off mirror 40' before being focused on analyzing detector 36.

Although the preferred embodiments have been described with reference to mirrors 24, 38, 40 and 40', it will be readily appreciated by those having skill in the art that similar optical functions may be performed with lenses. Additionally, preferred wavelengths have been set forth, but the invention is operable with detectors which are responsive to both measuring and reference radiation having wavelengths anywhere in the electromagnetic spectrum. Although not a preferred embodiment, it is also contemplated to provide separate radiation sources for the measuring and reference radiation.

The preferred method for quantifying a sample gas utilizing a photometric apparatus will now be described. A source means able to produce both reference radiation at an associated wavelength band and measuring radiation at an associated wavelength band is provided. Means for transmitting substantially only the measuring radiation is placed in the optical path of the source radiation, establishing "measuring mode". The transmitted measuring radiation is then split into an analyzing information channel and a normalizing information channel by inserting beam splitting means in the optical path. The measuring radiation traveling in the normalizing information channel is directed to a normalizing detector which generates normalizing detector response, $N_M$. The measuring radiation traveling in the analyzing information channel is directed to an analyzing detector which generates analyzing detector response, $A_M$. The sample interaction that the measuring radiation has in the normalizing information channel is substantially different than the sample interaction that the measuring radiation has in the analyzing information channel. One preferred method of establishing the difference in sample interaction is to increase the length of the optical path the measuring radiation travels through the sample material compared to the length of the optical path that the measuring radiation travels in the normalizing information channel. Another preferred method is directing a first portion of the measuring radiation to the normalizing detector without any sample material interaction, and directing a second portion of the measuring radiation through the sample material to the analyzing detector.

Means for transmitting substantially only the reference radiation is then placed in the optical path of the source radiation, establishing "normalizing mode". Again, the transmitted radiation, in this case reference radiation, is then split into an analyzing information channel and a normalizing information channel by the beam splitting means. The reference radiation traveling in the normalizing information channel is directed to a normalizing detector which generates normalizing detector response, $N_R$. The reference radiation traveling in the analyzing information channel is directed to an analyzing detector which generates analyzing detector response, $A_R$. The optical paths that the reference radiation travels in the analyzing information channel and the normalizing information channel are essentially coincident with the respective paths traveled by the measuring radiation.

The detector responses, $N_M$, $A_M$, $N_R$, and $A_R$ are processed to obtain a sample quantity response, f(mq).

It will be readily apparent the method works equally well if the apparatus is operated in "normalizing mode" prior to "measuring mode".

The invention has been described with reference to a preferred embodiment. Obviously, modifications and alterations will occur to others upon a reading and understanding of this specification. It is intended to include all such modifications and alternations in so far as they come within the scope of the appended claims or the equivalence thereof.

Having thus described the invention, it is now claimed: What is claimed is:

1. An apparatus for quantifying a sample gas homogeneously distributed within a sampling zone comprising:
   a radiation source for emitting source radiation including measuring radiation associated with a first wavelength band of approximately 4.26 microns and reference radiation associated with a second wavelength band of approximately 3.7 microns;
   a first mirror being positioned to collect the source radiation and direct the source radiation toward a first focal point;
   a filter assembly comprising a first optical filter being able to substantially transmit reference radiation and substantially block non-reference radiation and a second optical filter being able to substantially transmit measuring radiation and substantially block non-measuring radiation, the filter assembly being located between the first mirror and the first focal point;
   filtering means for selectively positioning the filter assembly so that one of the optical filters lies in the initial optical path of the source radiation whereby filtered radiation selectively continues in the optical path;
   beam splitting means for splitting the filtered radiation into first and second portions, the first portion being directed along a normalizing optical path and the second portion being directed along an analyzing path, the analyzing path passing at least partially through the sampling zone, the first and second portions having substantially different sample interaction;
   a focusing mirror being positioned in the analyzing path and having an axial opening therein, the axial opening being placed at the first focal point, the focusing mirror having a second focal point;
   a collimating mirror having an axial opening therein, the axial opening being positioned at the second focal point, the collimating mirror collecting and collimating the filtered radiation after it passes through the axial opening in the focusing mirror, the collimating mirror directing the filtered radiation back to the focusing mirror, the focusing mirror directing the radiation to the second focal point;
   a normalizing detector positioned in the normalizing optical path for detecting the first portion and creating a normal detector response, $N_R$, when the filtered radiation is the reference radiation and creating a normal detector response, $N_M$, when the filtered radiation is the measuring radiation;
   an analyzing detector being positioned in the analyzing optical path near the second focal point for detecting the second portion and creating an analyzing detector response, $A_R$, when the filtered radiation is the reference radiation and creating an analyzing detector response, $A_M$, when the filtered radiation is the measuring radiation; and,
   means for processing the normal detector responses and the analyzing detector responses to quantify the sample gas.

2. An apparatus for quantifying a sample gas homogeneously distributed within a sampling zone comprising:
   a radiation source for emitting source radiation including measuring radiation associated with a first wavelength band and reference radiation associated with a second wavelength band;
   means for directing the source radiation along an initial optical path;
   a filter assembly comprising a first optical filter being able to substantially transmit reference radiation and substantially block non-reference radiation and a second optical filter being able to substantially transmit measuring radiation and substantially block non-measuring radiation;
   filtering means for selectively positioning the filter assembly so that one of the optical filters lies in the initial optical path of the source radiation whereby filtered radiation selectively continues in the optical path;
   beam splitting means for splitting the filtered radiation into first and second portions, the first portion being directed along a normalizing optical path and the second portion being directed along an analyzing path, the analyzing path passing at least partially through the sampling zone, the first and second portions having substantially different sample interaction;
   a first mirror being positioned to collect the source radiation and direct the source radiation toward a first focal point, the first focal point being located downstream from the filter assembly;

a focusing mirror having an axial opening therein, the axial opening being placed at the first focal point, the focusing mirror having a second focal point;

a collimating mirror having an axial opening therein, the axial opening being positioned at the second focal point, the collimating mirror directing the filtered radiation back to the focusing mirror, the focusing mirror directing the radiation to the second focal point;

a normalizing detector positioned in the normalizing optical path for detecting the first portion and creating a normal detector response, $N_R$, when the filtered radiation is the reference radiation and creating a normal detector response, $N_M$, when the filtered radiation is the measuring radiation;

an analyzing detector positioned in the analyzing optical path for detecting the second portion and creating an analyzing detector response, $A_R$, when the filtered radiation is the reference radiation and creating an analyzing detector response, $A_M$, when the filtered radiation is the measuring radiation; and, means for processing the normal detector responses and the analyzing detector responses to quantify the sample gas.

3. The apparatus of claim 2 wherein the analyzing detector is positioned near the second focal point.

4. A method for quantifying a sample gas comprising the steps of:

providing source means for producing a measuring radiation associated with a first wavelength band and a reference radiation associated with a second wavelength band;

providing means for substantially transmitting only measuring radiation along an optical path;

splitting the transmitted measuring radiation into first and second portions;

directing the first portion of measuring radiation to a normalizing detector in a normalizing information channel to obtain normalizing detector response, $N_M$;

directing the second portion of measuring radiation to an analyzing detector in an analyzing information channel to obtain analyzing detector response, $A_M$, the second portion of measuring radiation making a plurality of optical passes through the sample gas;

providing means for transmitting substantially only reference radiation along an optical path;

splitting the reference radiation into first and second portions;

directing the first portion of reference radiation to the normalizing detector in the normalizing information channel to obtain a normalizing detector response, $N_R$, the first portions of measuring and reference radiation having substantially identical first optical paths relative to the sample gas;

directing the second portion of reference radiation to the analyzing detector in the analyzing information channel to obtain analyzing detector response $A_R$, the second portions of measuring and reference radiation having substantially identical second optical paths relative to the sample gas, the first and second optical paths being substantially different; and, processing the detector responses to obtain a sample quantity response, f(mq).

* * * * *